United States Patent
Kubota et al.

[11] Patent Number: 5,831,723
[45] Date of Patent: Nov. 3, 1998

[54] PARTICLE ANALYZER

[75] Inventors: Fumio Kubota, Nishinomiya; Hideo Kusuzawa, Kobe, both of Japan

[73] Assignee: TOA Medical Electronics Co., Ltd., Hyogo, Japan

[21] Appl. No.: 832,559

[22] Filed: Apr. 2, 1997

[30] Foreign Application Priority Data

Apr. 3, 1996 [JP] Japan .................................. 8-081621

[51] Int. Cl.$^6$ .................................................. G01N 15/14
[52] U.S. Cl. .............................................. 356/73; 356/23
[58] Field of Search ........................................ 356/73, 23

[56] References Cited

U.S. PATENT DOCUMENTS 5,150,313  9/1992  van den Engh et al. .

FOREIGN PATENT DOCUMENTS 0539022   4/1993   European Pat. Off. .
0551010   7/1993   European Pat. Off. .
0679889  11/1995   European Pat. Off. .
5-180751  7/1993   Japan .

OTHER PUBLICATIONS

John A. Steinkamp et al.; "Improved Multilaser/Multiparameter Flow Cytometer for Analysis and Sorting of Cells and Particles"; *Review of Scientific Instruments*; 1991 Nov.; pp. 2751–2764.

*Primary Examiner*—Vincent P. McGraw

[57]  ABSTRACT

A particle analyzer includes a sheath flow cell for converting a particle containing sample into a sample flow, a first light source for illuminating the sample flow by a continuous light, a light detecting element for detecting a light emitted from a particle illuminated by the first light source and for converting the light into a particle signal indicative of a characteristic of the particle, a second light source for illuminating the sample flow by a momentary light, an imaging device for capturing an image of a particle illuminated by the second light source, an analyzing section for performing particle analysis by employing the particle signal and the image of the particle as analysis data for analyzing the particle, and an inhibiting section for inhibiting the analyzing section from employing, as the analysis data, the particle signal obtained when the second light source illuminates the sample flow.

5 Claims, 5 Drawing Sheets

PARTICLE ANALYZER

BACKGROUND OF THE INVENTION

1. Field of the Invention

The present invention relates to a particle analyzer, and more particularly to a particle analyzer comprising a particle imaging system for capturing images of particles and a particle detecting system for optically detecting characteristics of the particles.

2. Description of the Related Art

A conventional particle analyzer employs a particle detecting system for detecting particles in a detecting area provided on the upstream part of a sample flow including particles such as blood corpuscles or cells, and a particle imaging system for capturing images of the particles in an imaging area provided on the downstream part of the sample flow.

Depending on a particle signal obtained from the particle detecting system, it is judged whether or not the particles detected in the detecting area are to be captured. When the particles to be captured reach the imaging area, the images of the particles are captured. A photodetector of the particle detecting system includes a shutter. When a light is emitted from a light source of the imaging system, the shutter is closed in such a manner that the light is not incident on the photodetector (see Japanese Unexamined Patent Publication No. Hei 5(1993)-180751, for example).

In the particle analyzer, however, when an image of a first one of particles flowing together with the sample flow is captured in the imaging area, the shutter is closed. If a next particle has already reached the detecting area the moment the shutter is closed or opened, a light emitted from the next particle is partially intercepted by the shutter and received by the photodetector. For this reason, a correct particle signal cannot be obtained for the next particle.

The particle analyzer according to the prior art is not directed to obtain a correct particle signal but is directed to capture images of particles. Therefore, it does not matter if the correct particle signal cannot be obtained.

On the other hand, the present invention is also directed to analyze particles based on a correct particle signal. Accordingly, an incorrect particle signal becomes a problem.

SUMMARY OF THE INVENTION

In consideration of the foregoing, it is an object of the present invention to provide a particle analyzer capable of analyzing particles with high precision by capturing images of the particles and removing incorrect particle signals to detect only correct particle signals.

The present invention provides a particle analyzer comprising a sheath flow cell for converting a particle containing sample into a sample flow, a first light source for illuminating the sample flow by a continuous light, a light detecting element for detecting a light emitted from a particle illuminated by the first light source and for converting the light into a particle signal indicative of a characteristic of the particle, a second light source for illuminating the sample flow by a momentary light, an imaging device for capturing an image of a particle illuminated by the second light source, an analyzing section for performing particle analysis by employing the particle signal and the image of the particle as analysis data for analyzing the particle, and an inhibiting section for inhibiting the analyzing section from employing, as the analysis data, the particle signal obtained when the second light source illuminates the sample flow.

DESCRIPTION OF THE PREFERRED EMBODIMENTS

Figure 1:
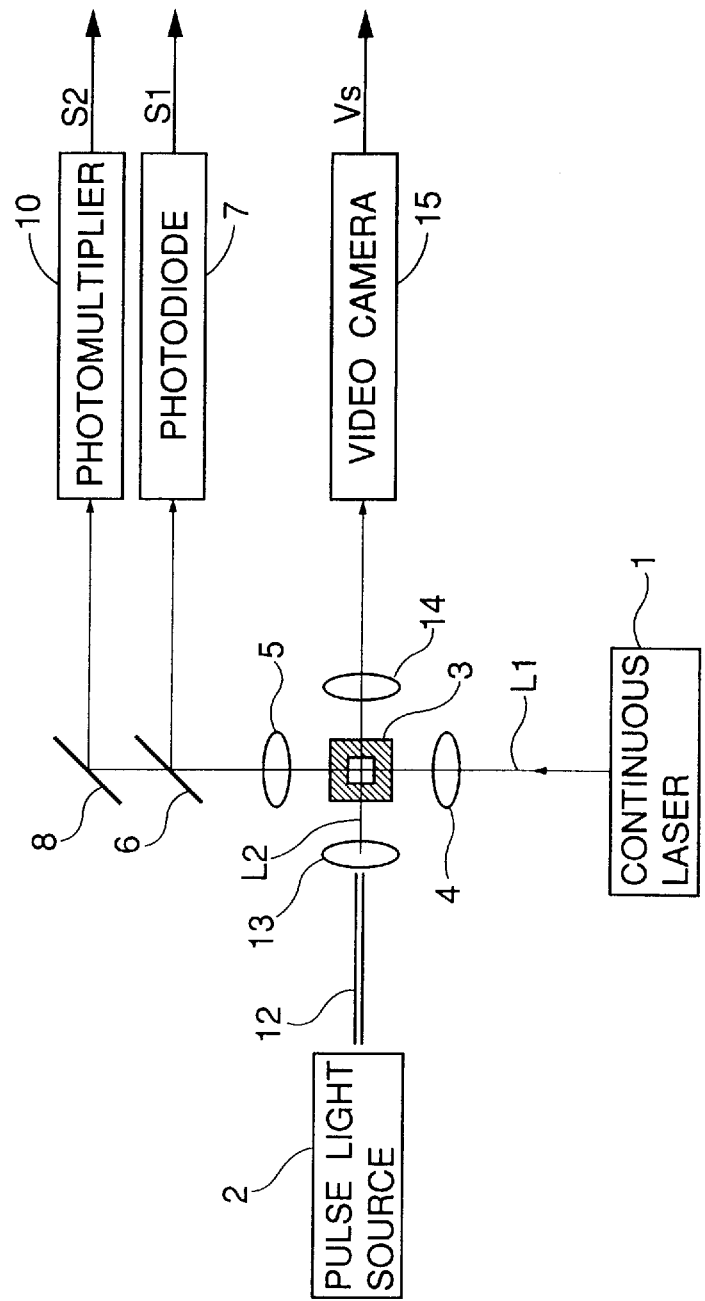
FIG. 1 is a diagram showing a structure of an optical system according to an embodiment of the present invention.

In the sheath flow cell according to the present invention, a sample including particles is enveloped in a sheath solution to flow so that a thin flow of a sample solution can be formed by hydrodynamic effects. A well-known sheath flow cell and sheath solution can be used for the present invention.

Examples of particles to be measured according to the present invention mainly include blood corpuscles and cells contained in blood and urine, and may be microorganisms such as yeasts or lactic bacterias, industrial powders and the like.

In order to classify kinds of the blood corpuscles and cells, nucleic acid and the like contained in the corpuscles or cells can be sometimes reacted with a specific fluorescent reagent and measured for a fluorescent intensity of the resultant.

For example, a continuous light source such as a laser, a halogen lamp or a tungsten lamp which continuously irradiates a light can be used for the first light source. The photodetecting element can be formed by a photodiode, a phototransistor or a photomultiplier tube, for example. More specifically, the particle signal is data such as a forward scattered light intensity or a fluorescent intensity which represents characteristics of particles.

An intermittent light source such as a pulse laser (for example, 7000 series manufactured by Spectra-Physics Co., Ltd.) or a multistroboscope (for example, DSX series manufactured by Sugawara Laboratories, Inc. Japan) which intermittently irradiates a light can be used for the second light source.

While the imaging device for capturing images of particles may be a conventional video camera for capturing two-dimensional images, it may include an image intensifier for amplifying feeble fluorescent images. Furthermore, the image intensifier may include shutter means.

The analyzing section can be formed by a microcomputer including a CPU, a ROM and a RAM.

The inhibiting section plays so as not to adopt, as data for particle analysis, a particle signal obtained from the photodetecting element when emitting a light from the second light source, and may be implemented by a hardware or software. For example, in the case where the analyzing section includes an A/D converter for A/D converting the particle signal obtained from the photodetecting element into the data for particle analysis, the inhibiting section is preferably a circuit for stopping operation for inputting the particle signal to the A/D converter or A/D converting operation temporarily (for a predetermined period of time) corresponding to light emission of the second light source.

In the case where the analyzing section stores the particle signal in a storing section (memory) and then analyzes the particle signal, the inhibiting section may be a circuit for inhibiting the data for particle analysis obtained at the time of the light emission of the second light source from being stored.

Furthermore, the inhibiting section may include a flag adding section for adding an identifier (a flag bit) to the particle signal obtained at the time of the light emission of the second light source, while the analyzing section is constructed to play so as not to adopt, as the data for particle analysis, the particle signal having the identifier.

Figure 2:
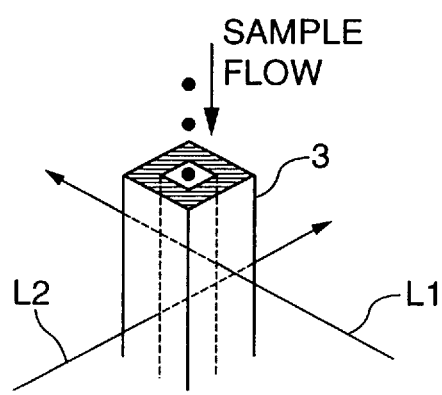
FIG. 2 is a perspective view showing a main part in FIG. 1.

FIGS. 1 and 2 show an optical system according to an embodiment of the present invention. In the present embodiment are provided two light sources, that is, a continuous laser beam source 1 (first light source) for detecting a scattered light and a fluorescence, and a pulse light source 2 (second light source) for capturing cell images.

As shown in FIG. 2, lights L1 and L2 emitted from the light sources 1 and 2 intersect at an angle of 90 deg. such that they are orthogonal to each other with respect to a square type sheath flow cell 3 (in which a sample flows perpendicularly to a paper in FIG. 1).

The pulse light source 2 for capturing cell images irradiates a light on the sample flow in the sheath flow cell 3 on a downstream side apart from an irradiation position of the continuous laser beam source 1 (for example, by about 20 micrometers).

A cell suspension treated with a proper fluorescent reagent is led to the sheath flow cell 3 so that the sample flow throttled thinly by the sheath solution is formed. The continuous laser beam L1 is throttled thinly by a condenser lens 4 and is irradiated on the sample flow.

When cells flow to an irradiation region, a scattered light and a fluorescence emitted from the cells are gathered by an objective lens 5. The scattered light is reflected by a dichroic mirror 6 and is received by a photodiode 7. The fluorescence is reflected by a dichroic mirror 8 and is received and multiplied by a photomultiplier 10.

Figure 3:
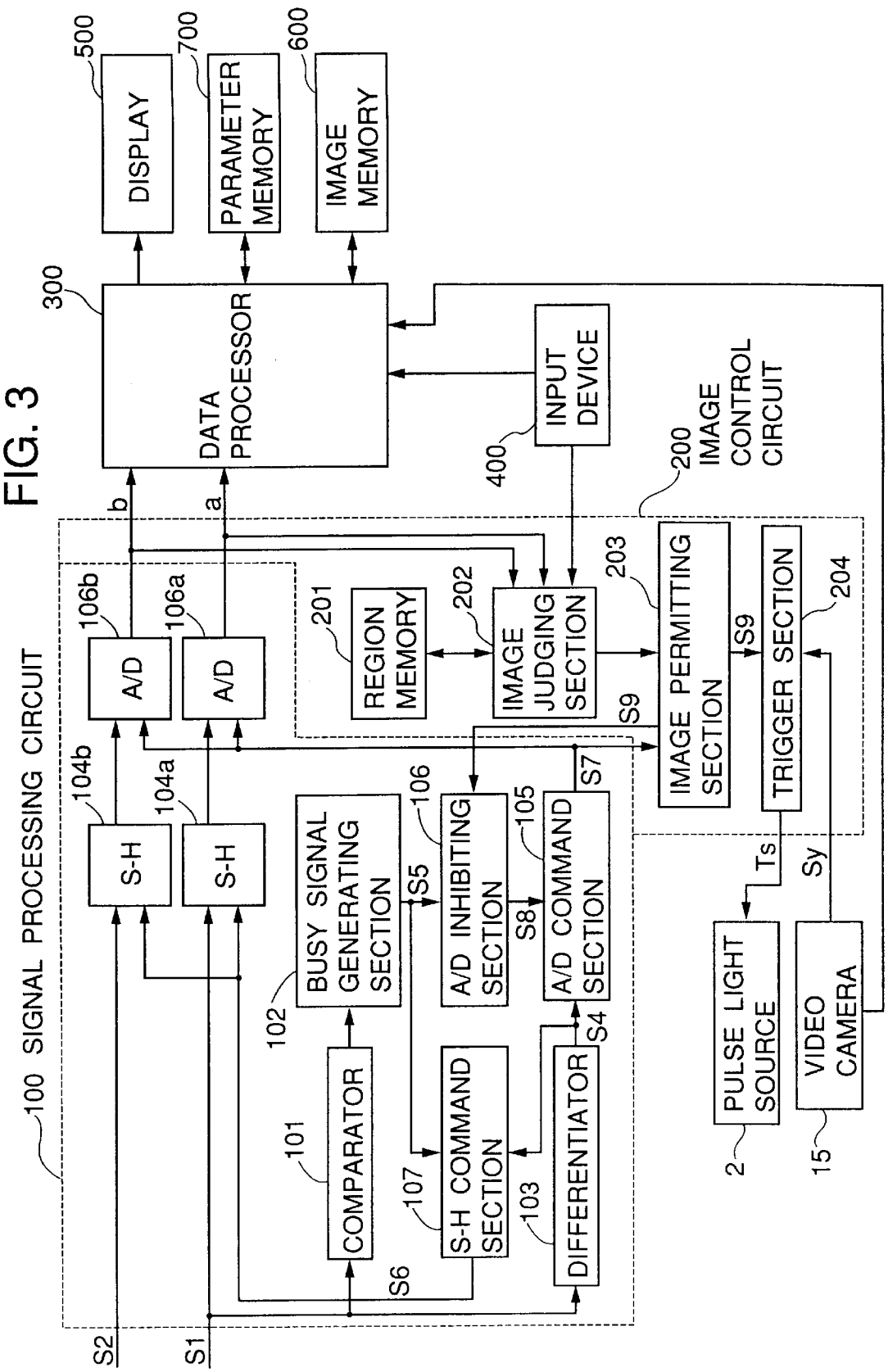
FIG. 3 is a block diagram showing a signal processing system according to the embodiment of the present invention.

FIG. 3 shows a structure of a signal processing system according to the present embodiment. A scattered light intensity signal S1 and a fluorescence intensity signal S2 detected by the photodiode 7 and the photomultiplier 10 are inputted to a signal processing circuit 100, and two characteristic parameters of a scattered light intensity "a" and a fluorescence intensity "b" are obtained by A/D converting information on a height of each detecting signal pulse.

In an image control circuit 200, an image judging section 202 identifies the kind of each cell in real time by using the parameters and performs control in such a manner that only cells of kinds specified as objects to be imaged by an input device 400 can be selected and imaged in advance.

More specifically, a characteristic parameter of a cell is compared, in real time, with that of the cell of a kind to be imaged. As a result, if it is judged that the cell is to be imaged, a light emitting trigger signal Ts for capturing an image of the cell is sent to the pulse light source 2.

The pulse light source 2 emits a light by the light emitting trigger signal Ts in a moment (for about several tens nanoseconds). Also in the case where a speed of the sample flow is high, for example, several ms/sec, images of flowing particles can be captured without blurring.

As shown in FIG. 1, a pulse light is led to the flow cell 3 by an optical fiber 12, is throttled thinly by a condenser lens 13 and is irradiated on the sample flow. By irradiating the pulse light through the optical fiber 12, a coherency of the pulse light is lowered so that a cell image having less diffracted fringe can be captured.

The image of the pulse light transmitted through the sample flow is formed on a light receiving face of a video camera 15 by a projection lens 14 so that a transmitted light image of the cell is captured. An image signal Vs is sent from the video camera 15 to a data processor 300 shown in FIG. 3, and is stored and retained as a digital image in an image memory 600.

The characteristic parameters "a" and "b" of the scattered light intensity, the fluorescence intensity and the like are inputted to the data processor 300, and are stored in a parameter memory 700. The data processor 300 analyzes a scattergram (two-dimensional frequency distribution) obtained by combination of the images and the parameters.

The input device 400 includes a keyboard and a mouse, and serves to specify a region of the scattergram and to set the number of imaging times in each regions. The reference numeral 500 denotes a display for displaying the scattergram, particle images, results of analysis and the like based on commands sent from the input device 400 and setting conditions.

In the present invention, the kinds of the cells to be imaged and the like can be preset to the scattergram displayed by the display 500. An example will be described below with reference to FIG. 4.

Figure 4:
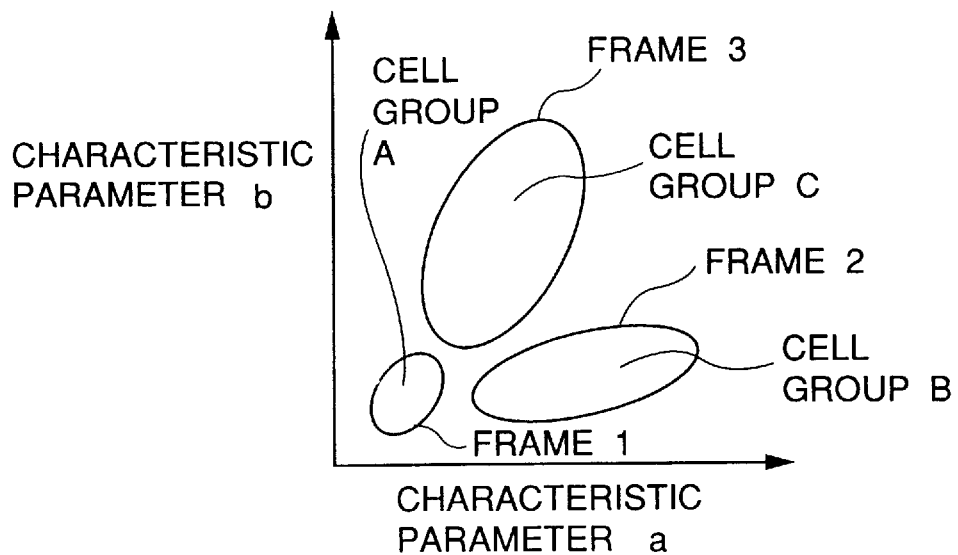
FIG. 4 is a chart showing an example of a displayed scattergram.

The scattergram shown in FIG. 4 assigns X and Y axes to values of the characteristic parameters "a" and "b" by the input device 400, respectively. It is assumed that a cell group A is distributed in a region of a frame 1, a cell group B is distributed in a region of a frame 2, and a cell group C is distributed in a region of a frame 3.

In order to select and image only the cell group B, for example, the input device 400 is used to enclose the cell group B by the frame 2. The image control circuit 200 judges whether or not the values of the characteristic parameters of the cells obtained by the signal processing circuit 100 are in the region of the frame 2 of the scat ergram shown in FIG. 4. If the values of the characterisic parameters "a" and "b" are data in the same region, the pulse light source 2 is caused to emit a light to capture an image of the cell.

The image control circuit 200 includes a memory 201 for registering distribution regions in which the values of the characteristic parameters assigned to the X and Y axes of the scattergram are set as address inputs in order to judge whether or not the characteristic parameters of the cells are data in the specified frames.

Figure 5:
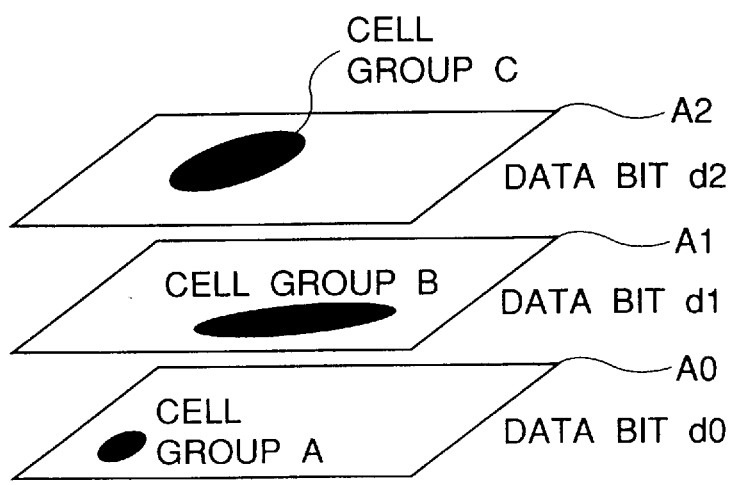
FIG. 5 is a diagram showing a bit map of a memory for registering distribution regions corresponding to FIG. 4.

Two-dimensional coordinates (scattergram) of the two characteristic parameters are imaged in memory regions A0, A1 and A2 as shown in FIG. 5. Data bits in the memory regions (addresses) corresponding to the regions in the respective frames set on the scattergram are preset to 1.

In an example shown in FIG. 4, a data bit d0 is caused to correspond to the frame 1, and the data bit d0 in the memory region corresponding to the frame 1 is set to 1. Similarly, the frames 2 and 3 are caused to correspond to data bits d1 and d2 respectively, and the data bits in the memory regions corresponding to the respective frames are set to 1.

In FIG. 5, a data bit on an address corresponding to a black-colored memory space is set to 1, and a data bit on a memory address corresponding to a region on the outside of the frame is set to 0.

Thus, the memory 201 for registering distribution regions is preset to perform registration before imaging. In this case, if a characteristic parameter of a cell is obtained during a measuring period, the contents (8-bit data) of the memory having a value of the characteristic parameter as a memory address are output immediately. The image judging section 202 can immediately judge a cell group to which the cell belongs depending on whether each bit of the data is 1 or 0.

For example, in the case where the characteristic parameter is the 8-bit data, a memory having an 8 bit×2=16 bit address space, that is, a memory having a capacity of 64k×8 bits is used as the memory for registering distribution regions.

Figure 6:
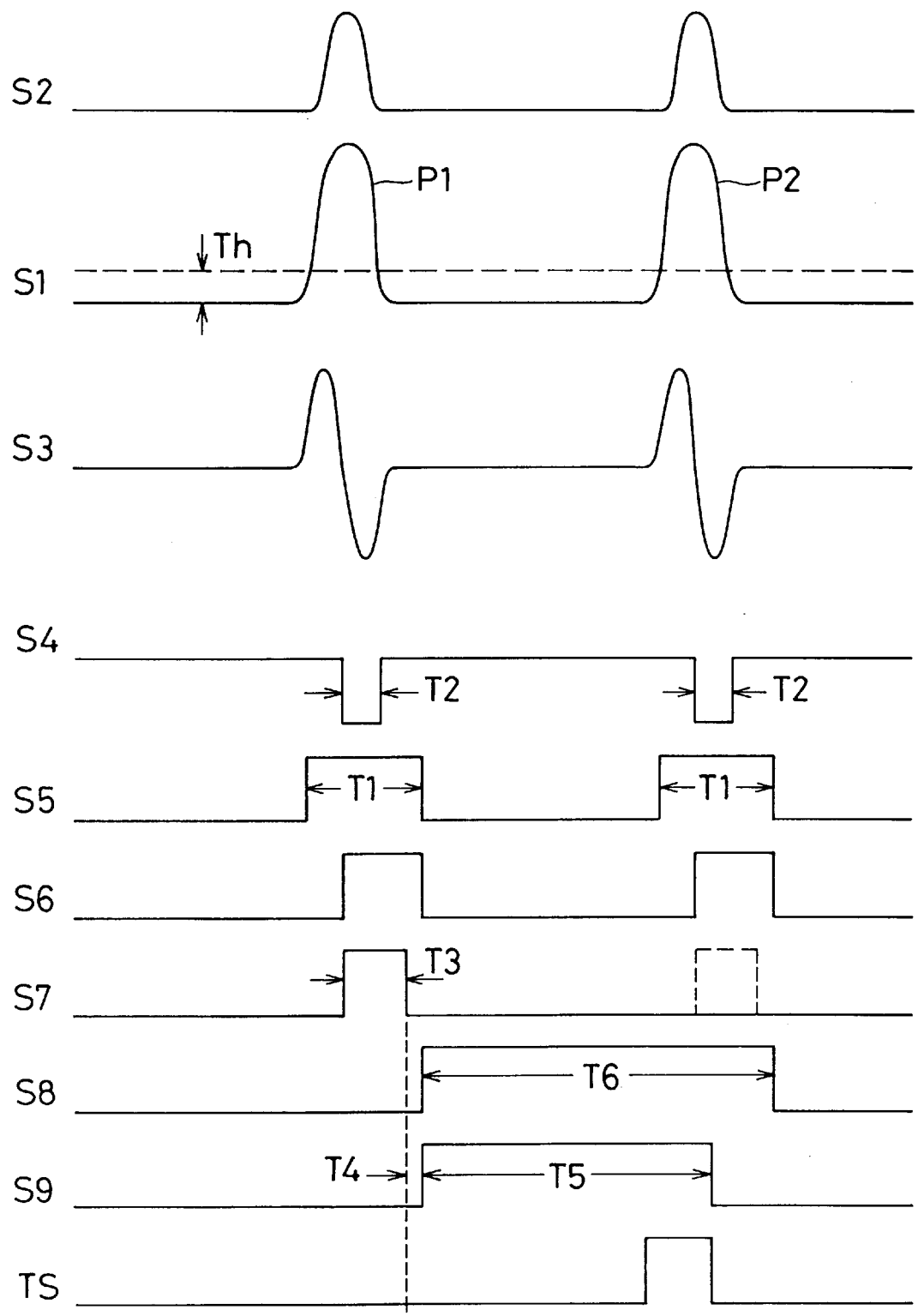
FIG. 6 is a timing chart showing operation of the signal processing system according to the embodiment of the present invention.

Furthermore, operation of the signal processing circuit 100 and the image control circuit 200 shown in FIG. 3 will be described in detail with reference to a timing chart shown in FIG. 6.

A signal S1 is changed to continuous pulses P1, P2, ... corresponding to first, second, ... particles flowing in the sheath flow cell 3 in order. First of all, the pulse P1 is compared with a threshold Th by a comparator 101. If the pulse P1 exceeds the threshold Th, a busy signal generating section 102 sets a particle busy signal S5 High for a predetermined time T1 after that time.

A differentiator 103 outputs a signal S4 set Low for a predetermined time T2 after the signal S1 is differentiated and a differential value S3 is set to 0, that is, the signal S1 reaches a peak.

An S-H command section 107 outputs a signal S6 set High from the fall of the signal S4 to that of the busy signal S5 to sample-and-hold circuits 104a and 104b to sample peak values of the signals S1 and S2 and hold them until the busy signal S5 falls.

An A/D command section 105 outputs, to A/D converting sections 106a and 106b, a signal S7 for sending a command to perform A/D conversion for a predetermined time T3 after the fall of the signal S4. Consequently, the signals S1 and S2 are A/D converted and changed into the characteristic parameters a and b.

After the signal S7 falls, that is, the A/D conversion is completed, the image judging section 202 judges whether or not the image of the particle is to be captured based on the obtained characteristic parameters a and b, and inputs a result of judgment to an image permitting section 203 at a time T4.

If the image of the particle is to be captured, the image permitting section 203 outputs an image permitting signal S9 to a trigger section 204 for a predetermined time T5. When the trigger section 204 detects that the time T5 is an even field period in response to a synchronous signal Sy sent from the video camera 15, it outputs a light emitting trigger signal TS.

An A/D inhibiting section 106 outputs, to the A/D command section 105, an A/D inhibiting signal S8 which rises simultaneously with rise of the signal S9, and inhibits the A/D command section 105 from outputting the signal S7, that is, the signals S1 and S2 from being A/D converted at a period T6 in which the signal S8 is High.

The signal S8 is usually set to be the same as the signal S9 (T5=T6). If the busy signal S5 having a second pulse P2 rises when the signal S9 falls, the A/D inhibiting section 106 extends the fall of the signal S8 up to that of the signal S5 to inhibit the second particle signals S1 and S2 from being A/D converted.

Accordingly, even if the pulse light for imaging which is irradiated on the first particle is mixed into the photodiode 7 and the photomultiplier 10, the erroneous signals S1 and S2 are not detected as the characteristic parameters a and b of the second particle.

Thus, the data processor 300 sorts and analyzes particles based on the accurate characteristic parameters of particles and particle images.

Without inhibiting A/D conversion, signal input to the A/D converter may be inhibited by switch means such as an analog switch.

The inhibiting section may have a structure in which the A/D inhibiting section 106 does not use the signal S8 to be sent to the A/D command section 105 as a control signal to be sent to the A/D converters 106a and 106b but inputs the signal S8 to the data processor 300 and uses the signal S8 as a control signal for storage operation in the storing section. For example, a fetch of data of the characteristic parameters a and b obtained by A/D converting the signals S1 and S2 may be controlled by (positive and negative) logics of the inhibiting signal S8 obtained when the signal S7 falls, that is, the A/D conversion is completed, namely, operation for storing data in the parameter memory 700 may be controlled.

The inhibiting section may employ or unemploy the stored characteristic parameters a and b as data for particle analysis. For example, when the signal S7 falls, that is, the A/D conversion is completed, the inhibiting signal S8 is inputted to the data processor 300, positive and negative identifiers (flag bits) are added to the characteristic parameters a and b by the (positive and negative) logics of the inhibiting signal S8, and the characteristic parameters and corresponding identifiers are stored in the parameter memory 700. In the case where the characteristic parameters a and b are analyzed, they may be employed or unemployed as the data for particle analysis in accordance with the logic of the identifier.

According to the present invention, all particle detecting signals affected by the light emission of the light source for capturing images of particles are removed from the data for particle analysis. Therefore, particle analysis can be performed with high precision.

Although the present invention has fully been described by way of example with reference to the accompanying drawings, it is to be understood that various changes and modifications will be apparent to those skilled in the art. Therefore, unless otherwise such changes and modifications depart from the scope of the invention, they should be construed as being included therein.

What is claimed is:

1. A particle analyzer comprising:
   a sheath flow cell for converting a particle containing sample into a sample flow;
   a first light source for illuminating the sample flow by a continuous light;
   a light detecting element for detecting a light emitted from a particle illuminated by the first light source and for converting the light into a particle signal indicative of a characteristic of the particle;
   a second light source for illuminating the sample flow by a momentary light;
   an imaging device for capturing an image of a particle illuminated by the second light source; and
   an analyzing section for performing particle analysis by employing the particle signal and the image of the particle as analysis data for analyzing the particle; and
   an inhibiting section for inhibiting the analyzing section from employing, as the analysis data, the particle signal obtained when the second light source illuminates the sample flow.

2. The particle analyzer as defined in claim 1, wherein the analyzing section includes an A/D converter for A/D converting in advance the particle signal input from the light detecting element and the inhibiting section includes means for temporarily inhibiting converting operation of the A/D converter when the second light source illuminates the sample flow.

3. The particle analyzer as defined in claim 1, wherein the analyzing section includes an A/D converter for A/D converting in advance the particle signal input from the light detecting element and the inhibiting section includes means for temporarily inhibiting the light detecting element from inputting the particle signal to the A/D converter when the second light source illuminates the sample flow.

4. The particle analyzer as defined in claim 1, wherein the analyzing section includes an A/D converter for A/D converting in advance the particle signal input from the light detecting element and a storing section for storing the A/D converted particle signal, and the inhibiting section includes means for temporarily inhibiting the storing section from storing the A/D converted particle signal when the second light source illuminates the sample flow.

5. The particle analyzer as defined in claim 1, wherein the analyzing section includes:

an A/D converter for A/D converting in advance the particle signal input from the light detecting element;

identifier adding means for adding, to the A/D converted particle signal, an identifier indicative of the particle signal obtained when the second light source illuminates the sample flow; and a storing section for storing the A/D converted particle signal having the added identifier, the inhibiting section includes means for inhibiting the analyzing section from employing the particle signal having the identifier as the analysis data.

* * * * *